US006919071B2

(12) United States Patent
Choulot et al.

(10) Patent No.: US 6,919,071 B2
(45) Date of Patent: Jul. 19, 2005

(54) SUNSCREEN MILK

(75) Inventors: Jean-Christophe Choulot, Rambouillet (FR); Nathalie Petit, Saint-Martin-de-Nigelles (FR); Philippe Msika, Paris (FR); Patricia Ferraris, Raizeux (FR); Bernard Ribes, deceased, late of Dreux (FR); by Delphine Ribes, legal representative, Dreux (FR); by Jocelyne Hilaire, legal representative, Dreux (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

(21) Appl. No.: 10/240,718

(22) PCT Filed: Apr. 4, 2001

(86) PCT No.: PCT/FR01/01007

§ 371 (c)(1),
(2), (4) Date: Nov. 20, 2003

(87) PCT Pub. No.: WO01/74294

PCT Pub. Date: Oct. 11, 2001

(65) Prior Publication Data

US 2004/0191189 A1 Sep. 30, 2004

(30) Foreign Application Priority Data

Apr. 5, 2000 (FR) .............................. 00 04360

(51) Int. Cl.$^7$ ........................... A61K 7/42; A61K 7/00; C07H 1/00; C07H 15/00
(52) U.S. Cl. ........................... 424/59; 424/60; 424/400; 424/401; 536/1.11; 536/4.1; 536/18.3; 536/18.6; 536/102; 536/120; 536/124

(58) Field of Search ........................... 424/59, 60, 400, 424/401; 536/1.11, 120, 124, 102, 4.1, 18.3, 18.6

(56) References Cited

U.S. PATENT DOCUMENTS 5,188,831 A * 2/1993 Nicoll et al. ................ 424/401
5,428,142 A 6/1995 O'Lenick, Jr.
5,831,080 A 11/1998 Sejpka et al.

FOREIGN PATENT DOCUMENTS

EP 0 832 644 A 4/1998
EP 1 016 400 A 7/2000

OTHER PUBLICATIONS

Database, Caplus 'en Ligne, Retrieved from STN, Database Accession No. 1995:524043, XP–0021553307, JP 07–041416, Feb. 10, 1995.

* cited by examiner

Primary Examiner—Shelley A. Dodson
(74) Attorney, Agent, or Firm—Foley & Lardner, LLP

(57) ABSTRACT

The invention concerns a cosmetic or dermatological composition for protection against ultraviolet radiation, based on inorganic screening agent, characterized in that it comprises a water-in-oil emulsion containing a combination of at least a particulate inorganic sunscreening agent, selected among the group consisting of titanium dioxide, zinc oxide and mixtures thereof, and at least an emulsifier selected among the group consisting of silicone derivatives with glycosidic constituent, the particulate screening agent being homogeneously dispersed in the water-in-oil emulsion.

15 Claims, No Drawings

SUNSCREEN MILK

The present invention relates to a cosmetic or dermatological composition based on an inorganic screening agent, especially for children, having both a very good fluidity and an excellent broad-spectrum photoprotection. It has long been known that ultraviolet (UV) radiation emitted by sunlight not only has short-term visible effects (sunburn, tanning) but also causes long-term damage, in particular skin cancers. Appropriate sunscreens have been developed with children as particular targets since it has been shown that infancy is the key period in terms of memorization of the damage induced by incomplete photoprotection.

Historically, the first photoprotectants to have been used were synthetic screening agents which were soluble in oil or in water. These synthetic (organic) screening agents have the property of absorbing UV radiation in place of the skin but have a number of disadvantages, in particular a protection index which decreases with time and hours of sunshine (photoinstability), a penetration through the skin which poses the question of their fate in the body (in particular in children who are more sensitive to toxic effects) and finally an absorption of UVB or UVA radiation but extremely rarely both at the same time. During the past few years, inorganic screening agents have been used in particular for antisun products for children. Generally, they are titanium dioxide and zinc oxide which have the appearance of a white powder consisting of small particles of these pigments. While these already known products have certain advantages, in particular a lack of penetration through the skin, a stability to sunlight and over time a total inertia with respect to skin reactions (irritations, allergies and the like), a major disadvantage remained up until now for the user, namely a very white covering appearance and a difficulty in spreading, preventing effective protection from being obtained since either the user was not able to correctly apply the product to all the areas to be protected or they did not even seek to obtain such an application given that these very white and pasty covering products are not very esthetic in appearance and are not very convenient by nature, hence an incomplete photoprotection of the areas to be protected as a priority, that is to say the face, the neck, the shoulders, the hands and the feet. Indeed, the high viscosity of existing products results from a problem of nonhomogeneous dispersion of the inorganic pigments in the known excipients. Indeed, since a nonhomogeneous dispersion not only prevents good photoprotection (high protection index) but also a broad-spectrum photoprotection (UVB, short UVA and long UVA) from being obtained even in the areas where the application of the product may appear to be correct to the user, it was necessary, up until now, to compensate for this lack of homogeneity by increasing the quantity of inorganic pigment, and therefore the viscosity of the product. An unsatisfactory solution for reconciling broad-spectrum photoprotection and lower viscosity consisted in particular in reducing the inorganic pigment load by replacing it with organic screening agents whose presence is nevertheless to be avoided in particular in products for children as explained above. It has now been observed, quite surprisingly and unexpectedly, that the combination of certain inorganic screening agents with certain emulsifying agents makes it possible to obtain a cosmetic or dermatological composition having both a very good fluidity and an excellent photoprotection which is furthermore of a broad spectrum, in the absence of the necessary presence of inorganic screening agents. The cosmetic or dermatological composition according to the invention thus provides, first of all, a spectacular surface protection, resulting in protection indices which may be higher than 70, as illustrated by the examples below, while exhibiting a very good fluidity, that is to say a viscosity which may be less than 100 Pa.s (100 000 centipoises) at 25° C.

In addition, this cosmetic or dermatological composition not only no longer has the disadvantage of a viscous or even pasty appearance, but also it exhibits total transparency (no whitening effect), a decisive advantage from the cosmetic point of view for a high-protection antisun product.

The subject of the present invention is thus a cosmetic or dermatological composition for protecting against ultraviolet radiation, based on an inorganic screening agent, characterized in that it comprises a water-in-oil emulsion containing a combination of at least one particulate inorganic screening agent, chosen from the group consisting of titanium dioxide, zinc oxide and mixtures thereof, and at least one emulsifying agent chosen from the group consisting of silicone derivatives with a glycosidic constituent comprising a number of glucose units of between 2 and 10, the particulate inorganic screening agent being homogeneously dispersed in the water-in-oil emulsion and its mean particle size being between 1 and 100 nanometers, and the particulate inorganic screening agent being present in an amount of 6 to 40% by weight.

For the purposes of the present invention, the expression silicone derivatives with a glycosidic constituent is understood to mean any silicone derivatives comprising a number of glucose units of between 2 and 10. As silicone derivative, $(C_2-C_{30})$alkylsilicones and amino$(C_2-C_{30})$alkylsilicones are preferred. Thus, among the silicone derivatives with a glycosidic constituent according to the present invention, there may be mentioned in particular the derivatives obtained by reacting dimethicone polymers with glucose polymers. As dimethicone polymers, there may be mentioned, by way of examples, aminobispropyldimethicone, aminopropyldimethicone, amodimethicone, cetyldimethicone, hexyldimethicone, octyldimethicone and stearyldimethicone.

In a particular embodiment of the composition according to the invention, the silicone derivative with a glycosidic constituent is the product of the reaction of octyldimethicone with a glucose polymer, called ethylhexyl dimethicone ethoxy glucoside (INCI name, ethylhexyl dimethicone ethoxy glucoside No. 528 in International Cosmetic Ingredients Dictionary and Handbook, $8^{th}$ edition).

According to the present invention, the composition may comprise, in addition, at least one other conventional emulsifying agent, in particular cyclodimethicone.

In a particular embodiment of the composition according to the invention, the proportion of emulsifying agent is between about 5 and about 30% by weight, relative to the total weight of the composition.

Among the titanium dioxides used as inorganic screening agent, there may be mentioned hydrophilic or hydrophobic titanium dioxides, preferably titanium dioxides doped with iron. Among the commercially available titanium dioxides, there may be mentioned, as hydrophilic dioxide, Titanium dioxide P 25 S (75% anatase and 25% rutile), as hydrophobic dioxide, Titanium dioxide T 805, as hydrophilic dioxide doped with iron, Titanium dioxide PF 2 and, as hydrophobic dioxide doped with iron, Titanium dioxide T 817, from the company DEGUSSA. The titanium oxides used in the present invention may also be synthesized according to the AEROSIL® process developed by the company DEGUSSA. This process involves in particular the cocalcination of the titanium and iron chlorides, $TiCL_4$ and $FeCl_3$ respectively, at high temperature and in the presence of an oxohydrogenated flame. The titanium oxides synthesized, doped with iron, have a mean BET surface area of 50 m$^2$/g and a mean particle size of 21 nm.

Accordingly, it has been demonstrated that the UVA and UVB absorbing capacity of titanium oxides increased with their dispersion. The introduction of iron during the synthesis process leads to the formation of mixed iron-titanium oxides in which the titanium oxide is more dispersed. Finally, the insertion of iron within a titanium oxide phase, predominantly of the anatase type, causes a modification of the semiconducting properties of the titanium oxide and therefore of these photochemical properties.

In one particular embodiment of the composition according to the invention, the particulate inorganic screening agent is a mixture of titanium dioxide doped with iron or of hydrophobic titanium dioxide and of zinc oxide.

According to the present invention, the fatty phase may also comprise other cosmetically or dermatologically acceptable fatty substances, in particular animal, vegetable or mineral oils and their analogs, fatty alcohol benzoates and fatty acid triglycerides.

According to the present invention, the aqueous phase comprises water and cosmetically or dermatologically acceptable hydrophilic compounds, among which there may be mentioned glycerine, and optionally organic solvents such as water-soluble lower alcohols.

The cosmetic or dermatological composition according to the invention has a viscosity of less than 100 Pa.s (100 000 centipoises) at 25° C., measured with a Brookfield viscometer.

As regards the impairment of the DNA of skin cells by UV radiation, its essential repair, which will limit the perpetuation of the damage, is controlled by the protein P53 which orders cell repair or destruction (apoptosis). During solar exposure, the P53 protein may become ineffective through mutation in the gene, hence the proliferation of abnormal cells whose recognition and control are brought about by the immune system (Langerhans cell), last rampart against the tumor process.

As regards photoimmunosuppression, recent studies have shown that UV radiation impairs the essential cells of skin immunity, the Langerhans cells. It destroys them or creates dysfunction by inhibiting their action of recognition and protection against foreign agents (bacteria, viruses, tumors, allergens).

These two attacks of the skin in depth, caused by the action of UV radiation, can result in the formation of skin cancers.

However, while most antisun products protect against UV radiation to a greater or lesser degree by preventing sunburn, the most recent studies suggest that their efficacy, in particular, against photoimmunosuppression induced by UV radiation is only partial and therefore a chronic immunosuppression can develop in the absence of visible sunburn and despite application of these antisun products.

Some epidemiological studies have even shown that the risk of skin cancers is higher in the users of sunscreens, a paradox which might be explained by the fact that the absence of sunburn would allow longer exposures and therefore would promote the invisible damage by UV radiation.

Accordingly, the composition according to the invention may comprise, in addition, at least one agent protecting against the immunosuppression induced by ultraviolet radiation, chosen from the group consisting of Aloe vera (extract of Aloe barbadensis), vitamin E, the unsaponifiable component of soybean oil and mixtures thereof, in a proportion advantageously of between about 0.05% and about 5% by weight, relative to the total weight of the composition.

The cosmetic or dermatological composition according to the invention may comprise, in addition, at least one agent protecting the DNA of skin cells, chosen from the group consisting of isoflavones and/or zinc salts, in a proportion advantageously of between about 0.01% and about 1% by weight, relative to the total weight of the composition, said salt being advantageously zinc gluconate.

The "isoflavones" which can be used according to this particular embodiment of the present invention are obtained by chemical synthesis or are natural substances extracted from natural products, in particular from plants such as soybean, clover, lupine, apple seeds and the like. Very often, the topical compositions according to the present invention contain, as isoflavones, a mixture of various isoflavones, but they may also be present in pure form in the context of the present invention. Moreover, the aglycone forms of the isoflavones and the glycosylated forms thereof are distinguishable. These various forms are most often present in the form of a mixture. They are illustrated by the following formulae. Aglycone forms, of formula:

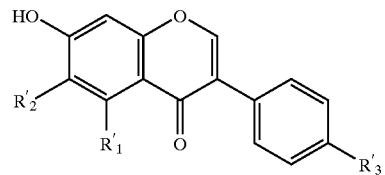

in which $R'_1$ represents a hydrogen atom or a hydroxyl group, $R'_2$ represents a hydrogen atom or a methoxy group and $R'_3$ represents a hydroxyl group.

Advantageously, according to the present invention, $R'_1$, $R'_2$ and $R'_3$ represent:

| $R'_1$ | $R'_2$ | $R'_3$ | Name of the compound |
|---|---|---|---|
| H | H | OH | Daidzein |
| OH | H | OH | Genistein |
| H | OCH$_3$ | OH | Glycitein |

Glycosylated forms, of formula:

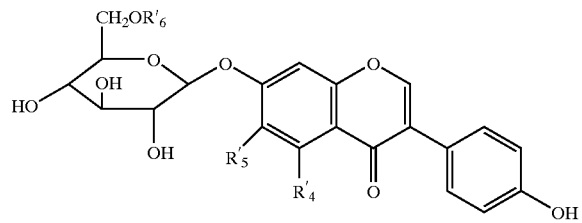

in which $R'_4$ represents a hydrogen atom or a hydroxyl group, $R'_5$ represents a hydrogen atom or a methoxy group and $R'_6$ represents a hydrogen atom.

Advantageously, according to the present invention $R'_4$, $R'_5$ and $R'_6$ represent:

| R'$_4$ | R'$_5$ | R'$_6$ | Name of the compound |
|--------|--------|--------|----------------------|
| H      | H      | H      | Daidzin              |
| OH     | H      | H      | Genistin             |
| H      | OCH$_3$| H      | Glycitin             |

The glycosylated forms of the isoflavones are the most abundant in nature.

The natural isoflavones such as genistein (1), daidzein or glycitein are preferred as isoflavones.

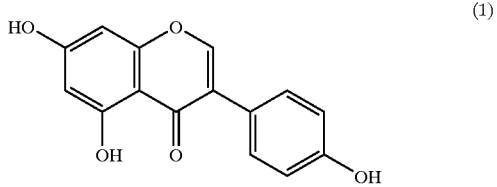
(1)

In particular, genistein or 4,5,7-trihydroxyisoflavone, which can be used according to the present invention, may be a product of plant, in particular soybean, origin titrating 85 to 90% by weight of genistein, in particular the product marketed by the company Buckton Scott under the name "genistein titrating 85%".

Thus, the cosmetic or dermatological composition according to the invention also has, in addition to this broad-spectrum photoprotection obtained by the specific inorganic screening agent—emulsifying agent combination, the advantage of a protective effect "in depth" against the impairment of the DNA of skin cells and more particularly against the phenomenon of photoimmunosuppression.

Of course, the composition according to the invention may also contain one or more conventional, lipophilic or hydrophilic, cosmetic adjuvants, in particular those which are already customarily used in the manufacture and the production of antisun cosmetic or dermatological compositions.

Thus, the cosmetic or dermatological composition according to the invention may comprise, in addition, at least one adjuvant chosen from the group consisting of ionic or nonionic thickeners, demulcents, antioxidants, opacifiers, stabilizers, emollients, insect repellents, organic sunscreens which are active in UV-A or UV-B (in particular when it is desired to use it in adults), moisturizers, vitamins, perfumes, preservatives, fillers, sequestrants, colorants and mixtures of these compounds.

It has been observed that the protection index (PI) of the cosmetic or dermatological composition according to the invention increases during storage, passing from 40 to 70 or from 20 to 30 after two months of storage, which could have some advantage during its use.

The cosmetic or dermatological composition according to the invention may be prepared by any method known to persons skilled in the art, in particular by mixing the various ingredients.

The cosmetic or dermatological composition according to the invention may be provided in the form of a cream, a milk, a gel, a gel cream, a lipstick, or in any other forms generally used in the cosmetic or dermatological field for the topical application of a water-in-oil emulsion, in particular those which are usually suitable for antisun cosmetic or dermatological compositions.

Another subject of the present invention consists in a method for the cosmetic or dermatological treatment of the skin intended to protect the skin against the harmfulness of and attack by ultraviolet radiation and which essentially consists in applying thereto an effective quantity of a cosmetic or dermatological composition as defined above. The compositions according to the invention may therefore be used in the treatment of pathologies linked to UVA and to UVB, in particular erythemas, acne, aging, immunosuppression, inflammation and the aggravation of other dermatological pathologies (acne, rosacea and the like).

The examples which follow illustrate the invention without limiting it to these specific embodiments.

Unless otherwise indicated, percentages indicated in the examples which follow are percentages by total weight of the composition.

EXAMPLE 1

Procedure for Antisun Products

1—Preparation of the Fatty Phase

The fatty phase (inorganic pigments, emulsifier and oil) is introduced into a reactor and homogenized with recycling in order to obtain good dispersion. This phase is heated to 60° C.

2—Preparation of the Aqueous Phase

In a stirred container, the gelling agent is dispersed in the aqueous phase containing the electrolytes, and then the active agents are added. This phase is heated to 60° C.

3—Emulsification

At 60° C., the aqueous phase is slowly poured (30 min) into the oil phase, while maintaining a fairly sustained stirring (using a turbine or a scraper) and the appearance of the emulsion is checked. The mixture is homogenized for 30 min, with recycling by cooling the product to 25° C.

The mixture is discharged and the product is then checked after allowing to stand for 1 hour in order to obtain an indication of its viscosity. The perfect uniformity of the emulsion is checked.

4—Measurement of the Viscosity

The viscosity is measured at 25° C. with a Brookfiled viscometer.

| Emulsifier | PI | Viscosity at 25° C. Pa · s (cp) |
|------------|----|----|
| PSA (cetyldimethicone polyols) | 35 | 200 (200 000) |
| PSA (cetyldimethicone polyols) | 20 | 60 (60 000) |
| Invention (Example 2) | 70 | 100 (100 000) |
| Invention (Example 3) | 50 | 60 (60 000) |
| Invention (Example 4) | 25 | 15 (15 000) |

Thus, for a similar protection index (PI), the compositions according to the invention possess a markedly lower viscosity than those of the compositions of the prior state of the art (PSA).

EXAMPLE 2

Formula with a Protection Index Greater than 70

| | |
|---|---|
| Octyldodecyl neopentapate | 15 to 30 |
| Titanium dioxide | 15 to 30 |
| Cyclomethicone | 10 to 20 |
| Water | 5 to 20 |
| Zinc oxide | 3 to 10 |
| Ethylhexyl dimethicone ethoxy glucoside | 1 to 10 |
| Caprylic/capric triglyceride | 1 to 10 |
| Glycerine | 1 to 10 |
| PEG45/dodecyl glycol copolymer | 1 to 10 |
| Cyclopentasiloxane | 1 to 10 |
| Sodium chloride | 1 to 5 |
| Unsaponifiable soybean oil | 1 to 5 |
| Dextrin palmitate | 1 to 5 |
| Stearalkonium hectorite | 1 to 5 |
| Phenoxyethanol | 0.5 |
| *Aloe barbadensis* extract | 0.1 to 10 |
| Zinc gluconate | 0.01 to 10 |
| Butylparaben | 0.06 |
| Ethylparaben | 0.04 |
| Propylparaben | 0.02 |

EXAMPLE 3

Formula with a Protection Index Greater than 50

| | |
|---|---|
| Water | 20 to 50 |
| Octyldodecyl neopentapate | 15 to 40 |
| Titanium dioxide | 10 to 20 |
| Cyclomethicone | 5 to 20 |
| Zinc oxide | 3 to 15 |
| Glycerine | 3 to 15 |
| Ethylhexyl dimethicone ethoxy glucoside | 3 to 15 |
| PEG-45/dodecyl glycol copolymer | 3 to 15 |
| Dextrin palmitate | 1 to 5 |
| Cyclopentasiloxane | 1 to 5 |
| Sodium chloride | 1 to 5 |
| Unsaponifiable soybean oil | 1 to 5 |
| Phenoxyethanol | 0.5 |
| *Aloe barbadensis* extract | 0.2 |
| Methylparaben | 0.1 to 10 |
| Zinc gluconate | 0.08 |
| Butylparaben | 0.01 to 10 |
| Ethylparaben | 0.04 |
| Propylparaben | 0.02 |

EXAMPLE 4

Formula with a Protection Index Greater than 25

| | |
|---|---|
| Water | 20 to 60 |
| Pentaerythrityl tetraoctanoate | 15 to 30 |
| Titanium dioxide | 1 to 10 |
| Cyclomethicone | 1 to 10 |
| Zinc oxide | 1 to 10 |
| C12–15 alkyl benzoate | 1 to 10 |
| Glycerine | 1 to 10 |
| Dicaprylyl ether | 1 to 10 |
| Cyclopentasiloxane | 1 to 10 |
| Ethylhexyl dimethicone ethoxy glucoside | 1 to 10 |
| Propylene glycol dioctanoate | 1 to 10 |
| Sodium chloride | 1 to 5 |
| PEG-45/dodecyl glycol copolymer | 1 to 5 |
| PEG-30 dipolyhydroxystearate | 1 to 5 |
| Unsaponifiable soybean oil | 1 to 5 |
| Dextrin palmitate | 1 to 5 |

-continued

| | |
|---|---|
| Phenoxyethanol | 0.5 |
| *Aloe barbadensis* extract | 0.1 to 10 |
| Methylparaben | 0.16 |
| Zinc gluconate | 0.01 to 10 |
| Butylparaben | 0.06 |
| Ethylparaben | 0.04 |
| Propylparaben | 0.02 |

The sum of the titanium dioxide and iron oxide contents being crystalline or equal to 6%

EXAMPLE 5

Formula with a Protection Index Greater than 70

| Ingredients | % by weight |
|---|---|
| Octyldodecyl neopentanoate | 15 to 30 |
| Titanium dioxide | 15 to 30 |
| Cyclomethicone | 10 to 20 |
| Water | 5 to 20 |
| Zinc oxide | 3 to 10 |
| Ethylhexyl dimethicone ethoxy glucoside | 1 to 10 |
| 2-Heptadecadienylfuran | 0.1 to 10 |
| 4,5,7-Trihydroxyisoflavone | 0.01 to 10 |
| Caprylic/capric triglyceride | 1 to 10 |
| Glycerine | 1 to 10 |
| PEG-45/dodecyl glycol copolymer | 1 to 10 |
| Cyclopentasiloxane | 1 to 10 |
| Sodium chloride | 1 to 5 |
| Unsaponifiable soybean oil | 1 to 5 |
| Dextrin palmitate | 1 to 5 |
| Stearalkonium hectorite | 1 to 5 |
| Phenoxyethanol | 0.5 |
| *Aloe barbadensis* extract | 0.2 |
| Zinc gluconate | 0.08 |
| Butylparaben | 0.06 |
| Ethylparaben | 0.04 |
| Propylparaben | 0.02 |

EXAMPLE 6

Formula with a Protection Index Greater than 50

| Ingredients | % by weight |
|---|---|
| Water | 20 to 50 |
| Octyldodecyl neopentanoate | 15 to 40 |
| Titanium dioxide | 10 to 20 |
| 2-Heptadecadienylfuran | 0.1 to 10 |
| 4,5,7-Trihydroxyisoflavone | 0.01 to 10 |
| Cyclomethicone | 5 to 20 |
| Zinc oxide | 3 to 15 |
| Glycerine | 3 to 15 |
| Ethylhexyl dimethicone ethoxy glucoside | 3 to 15 |
| PEG-45/dodecyl glycol copolymer | 3 to 15 |
| Dextrin palmitate | 1 to 5 |
| Cyclopentasiloxane | 1 to 5 |
| Sodium chloride | 1 to 5 |
| Unsaponifiable soybean oil (soybean glycine) | 1 to 5 |
| Phenoxyethanol | 0.5 |
| *Aloe barbadensis* extract | 0.2 |
| Methylparaben | 0.16 |
| Zinc gluconate | 0.08 |
| Butylparaben | 0.06 |
| Ethylparaben | 0.04 |
| Propylparaben | 0.02 |

EXAMPLE 7

Formula with a Protection Index Greater than 25

| Ingredients | % by weight |
|---|---|
| Water | 20 to 60 |
| Pentaerythrityl tetraoctanoate | 15 to 30 |
| Titanium dioxide | 1 to 10 |
| Cyclomethicone | 1 to 10 |
| Zinc oxide | 1 to 10 |
| (C12–15) alkyl benzoate | 1 to 10 |
| 2-Heptadecadienylfuran | 0.1 to 10 |
| 4,5,7-Trihydroxyisoflavone | 0.01 to 10 |
| Glycerine | 1 to 10 |
| Dicaprylyl ether | 1 to 10 |
| Cyclopentasiloxane | 1 to 10 |
| Ethylhexyl dimethicone ethoxy glucoside | 1 to 10 |
| Propylene glycol dioctanoate | 1 to 10 |
| Sodium chloride | 1 to 5 |
| PEG-45/dodecyl glycol copolymer | 1 to 5 |
| PEG-30 dipolyhydroxystearate | 1 to 5 |
| Unsaponifiable soybean oil | 1 to 5 |
| Dextrin palmitate | 1 to 5 |
| Phenoxyethanol | 0.5 |
| *Aloe barbadensis* extract | 0.2 |
| Methylparaben | 0.16 |
| Zinc gluconate | 0.08 |
| Butylparaben | 0.06 |
| Ethylparaben | 0.04 |
| Propylparaben | 0.02 |

EXAMPLE 8

Method of Determining the Sun Protection Factor

The sun protection level involves the erythemal response of the skin to ultraviolet radiation. It is expressed by the sun protection factor (SPF) which is the ratio of the energies necessary to induce a minimum erythemal response on the skin of volunteer subjects, protected or otherwise with the test product, using the ultraviolet radiation generally provided by an artificial source.

The method used is that of the COLIPA (European Cosmetic Toiletry and Perfumes Association) described in "The method for determining the sun protection factor, Ref: 94/289, October 1994).

The smallest dose which produces an erythema, called minimal erythemal dose (MED), either without protection (MEDn), or with protection (MEDp), is determined in each volunteer and the SPF is calculated as being the MEDp/MEDn ratio.

The compositions according to the invention have protection indices which may be as high as 70.

What is claimed is:

1. A cosmetic or dermatological composition for protecting against ultraviolet radiation, comprising a water-in-oil emulsion comprising a combination of at least one particulate inorganic screening agent, chosen from the group consisting of titanium dioxide, zinc oxide and mixtures thereof, and at least one emulsifying agent chosen from the group consisting of silicone derivatives with a glycosidic constituent comprising a number of glucose units of between 2 and 10, the particulate inorganic screening agent being homogeneously dispersed in the water-in-oil emulsion and having a mean particle size between 1 and 100 nanometers, and the particulate inorganic screening agent being present in an amount of 6 to 40% by weight, wherein the composition has a viscosity of less than 100 Pa.s (100 000 centipoises) at 25° C.

2. The cosmetic or dermatological composition according to claim 1, wherein the silicone derivative is chosen from $(C_2-C_{30})$alkylsilicones and amino$(C_2-C_{30})$alkysilicone-s.

3. The cosmetic or dermatological composition according to claim 2, wherein the silicone derivative with a glycosidic constituent is ethylhexyl dimethicone ethoxy glucoside.

4. The cosmetic or dermatological composition according to claim 1, further comprising cyclodimethicone.

5. The cosmetic or dermatological composition according to claim 1, wherein the proportion of emulsifying agent is between about 5 and about 30% by weight, relative to the total weight of the composition.

6. The cosmetic or dermatological composition according to claim 1, wherein the particulate inorganic screening agent is titanium dioxide doped with iron.

7. The cosmetic or dermatological composition according to claim 1, wherein the particulate inorganic screening agent is hydrophobic titanium dioxide.

8. The cosmetic or dermatological composition according to claim 1, wherein the particulate inorganic screening agent is a mixture of zinc oxide and one of a) titanium dioxide doped with iron or b) hydrophobic titanium dioxide.

9. The cosmetic or dermatological composition according to claim 1, further comprising at least one agent protecting against the immunosuppression induced by ultraviolet radiation, chosen from the group consisting of Aloe vera, vitamin E, the unsaponifiable component of soybean oil and mixtures thereof.

10. The cosmetic or dermatological composition according to claim 9, wherein the proportion of agent protecting against the immunosuppression induced by ultraviolet radiation is between about 0.05 and about 5% by weight, relative to the total weight of the composition.

11. The cosmetic or dermatological composition according to claim 1, further comprising at least one agent protecting the DNA of skin cells, chosen from the group consisting of isoflavones or zinc salts, both.

12. The cosmetic or dermatological composition according to claim 11, wherein the agent protecting the skin cells is zinc gluconate.

13. The cosmetic or dermatological composition according to claim 11, wherein the proportion of agent protecting the skin cells is between about 0.01 and about 1% by weight, relative to the total weight of the composition.

14. The cosmetic or dermatological composition according to claim 1, further comprising at least one adjuvant chosen from the group consisting of ionic or nonionic thickeners, demulcents, antioxidants, opacifiers, stabilizers, emollients, insect repellents, organic sunscreens which are active in UV-A or UV-B, moisturizers, vitamins, perfumes, preservatives, fillers, sequestrants, colorants and mixtures of these compounds.

15. A method for protecting skin against ultraviolet radiation comprising applying to the skin an effective quantity of the cosmetic composition according to any one of the preceding claims.

* * * * *